(12) United States Patent
Rodriguez

(10) Patent No.: US 6,919,493 B2
(45) Date of Patent: Jul. 19, 2005

(54) SUGAR-REGULATORY SEQUENCES IN ALPHA-AMYLASE GENES

(75) Inventor: Raymond L. Rodriguez, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 451 days.

(21) Appl. No.: 10/206,654

(22) Filed: Jul. 25, 2002

(65) Prior Publication Data

US 2003/0033634 A1 Feb. 13, 2003

Related U.S. Application Data

(63) Continuation of application No. 09/450,515, filed on Nov. 29, 1999, now Pat. No. 6,680,425, which is a continuation of application No. 09/046,858, filed on Mar. 24, 1998, now Pat. No. 6,048,973.
(60) Provisional application No. 60/042,376, filed on Mar. 24, 1997.

(51) Int. Cl.[7] .......................... C12N 5/10; C12N 15/82; C12N 15/90; C07H 21/04
(52) U.S. Cl. .................... 800/278; 435/320.1; 435/419; 536/24.1
(58) Field of Search .............................. 536/23.6, 24.1; 435/320.1, 419, 468; 800/278

(56) References Cited

U.S. PATENT DOCUMENTS 5,460,952 A   10/1995   Yu et al. ..................... 435/69.1

FOREIGN PATENT DOCUMENTS

| WO | WO 89/09267 | 10/1989 | .......... C12N/15/00 |
| WO | WO 95/03690 | 2/1995 | ............ A01H/1/04 |
| WO | WO 95/14099 | 5/1995 | ........... C12N/15/82 |

OTHER PUBLICATIONS

Benfey, et al., *Science* 250:959–966 (1990).
Chan, Ming–Tsair, et al., Novel Gene Expression System for Plant Cells Based on Induction of α–Amylase Promoter by Carbohydrate Starvation, *J. Biol. Chem.*, 269(26):17635–17641 (1994).

Chung–An Lu, et al., "Sugar Response Sequence in the Promoter of a Rice α–Amylase Gene Serves as a Transcriptional Enhancer," *J. Biol. Chem.*, 273(17):10120–10131 (1998).

Huang, N., et al., "Structural Organization and Differential Expression of Rice α–Amylase Genes," *Nuc. Acids Res.*, 18(23):7007–7014 (1990).

Huang, N., et al., "Classification and Characterization of the Rice α–Amylase Multigene Family," *Plant Mol. Biol.*, 14:655–668 (1991).

Huang, N., et al., "Metabolic Regulation of a α–Amylase Gene Expression in Transgenic Cell Cultures of Rice," *Plant Mol. Biol.*, 23:737–747 (19*93).

Hwang, Y.S., et al., "Three Cis–Elements Required for Rice α–Amylase Amy3D Expression During Sugar Starvation," *Plant Mol. Biol.*, 36:331–341 (1998).

Mitsunaga, Shin–Ichiro, et al., "Sequence–specific Interactions of a Nuclear Protein Factor with the Promoter Region of a Rice Gene for α–Amylase RAmy3D," *Nuc. Acids. Res.*, 22(11):1948–1953 (1994).

Thomas, Bruce, R., et al., "Gene Regulation and Protein Secretion from Plant Cell Cultures: the Rice α–Amylase System," *Advances in Plant Biotechnology*. 4:37–55 (1994).

*Primary Examiner*—Ashwin Mehta
(74) *Attorney, Agent, or Firm*—Townsend and Townsend and Crew LLP

(57) ABSTRACT

A chimeric plant promoter which is responsive to sugar depletion or deprivation is disclosed. The promoter includes a promoter element and, carried in the element, a heterologous sequence from the rice Amy3D that is responsive to sugar depletion. Also disclosed is a plant transfecting vector containing the sequence, and plant cell transfected with the vector.

15 Claims, 6 Drawing Sheets

SUGAR-REGULATORY SEQUENCES IN ALPHA-AMYLASE GENES

This application is a continuation of U.S. patent application Ser. No. 09/450,515, filed Nov. 29, 1999, now U.S. Pat. No. 6,680,425, issued Jan. 20, 2004 [now pending]; which is a continuation of application Ser. No. 09/046,858, filed Mar. 24, 1998, now U.S. Pat. No. 6,048,973, issued Apr. 11, 2000; which claims the priority of U.S. Provisional of Application No. 60/042,376; filed Mar. 24, 1997, now abandoned; which are incorporated herein by reference.

This invention was made with Government support under Grant No. IBN 94-08369, awarded by the National Science Foundation. The Government has certain rights in this invention.

FIELD OF THE INVENTION

The present invention relates to novel plant chimeric promoters that are responsive to sugar depletion conditions in a plant cell.

BACKGROUND OF THE INVENTION

The Amy3D and Amy3E genes are two sugar-regulated genes in the rice α-amylase family (Huang, N. et al., *Nucleic Acids Res.*, 18(23):7077 (1990)). Amy3D is expressed in seedlings in response to sugar depletion and is not expressed when sugar, such as glucose, concentrations are elevated. Further, Amy3D is upregulated strongly in cell culture under conditions of sugar depletion or sugar deprivation. Unlike many other α-amylase genes, Amy3D is not induced in response to gibberellic acid.

Metabolic regulation of Amy3D expression provides a signal mechanism to help control sugar production in the source tissues of germinating cereal seedling. Thus, the rate of starch breakdown is modulated in response to the rate at which the embryo axis can utilize sugar for its growth.

SUMMARY OF THE INVENTION

In one aspect, the invention includes a chimeric plant promoter for upregulating expression of a coding sequence operatively linked to the promoter, under conditions of sugar depletion or deprivation in a plant cell. The promoter includes a promoter element effective to express the coding sequence, under selected conditions and, carried in the promoter element, one or more of the following heterologous sequences which are responsive to (upregulated by) sugar depletion in plant cells: SEQ ID NO:1, SEQ ID NO:2, SEQ ID NO:3, SEQ ID NO:4, and combinations of these sequences. An exemplary combination is produced from sequences from SEQ ID NOS: 2 and 3, identified as SEQ ID NO:5.

In one embodiment the heterologous sequences is duplicated. In another embodiment, the promoter element is a monocot amylase-gene promoter, and the heterologous sequence is inserted in the promoter element at a position homologous to the position of the heterologous sequence in the rice Amy3D gene. Exemplary promoter elements are from the RAmy1A, RAmy1B, RAmy2A, RAmy3A, RAmy3B, RAmy3C, pM/C, gKAmy141, gKAmy155, Amy32b, and HV18 genes.

Also forming part of the invention is a method of enhancing the inducibility by sugar depletion or deprivation of a plant or plant-virus promoter in plant cells. The method includes introducing into a plant promoter or plant-virus promoter, one or more of the above heterologous sequences, to achieve at least a 2-fold greater sugar-depletion induction level over that of the unmodified promoter.

The promoter may be, for example, an α-amylase promoter from a monocot α-amylase gene, such as the RAmy1A, RAmy1B, RAmy2A, RAmy3A, RAmy3B, RAmy3C, pM/C, gKAmy141, gKAmy155, Amy32b, or HV18 genes. The promoter may be duplicated in the chimeric promoter. The plant may be a monocot plant.

In another aspect, the invention includes a vector for use in transforming a plant. The vector includes a chimeric gene having, operatively linked in sequence in a 5' to 3' direction, (i) the above chimeric plant promoter, (ii) a gene encoding a protein to be expressed, and (iii) a 3' untranslated terminator region. Also disclosed are plant cells transfected with the vector.

These and other objects and features of the invention will be more fully understood when the following detailed description of the invention is read in conjunction with the accompanying drawings.

DETAILED DESCRIPTION OF THE INVENTION

I. Definitions

Figure 1:
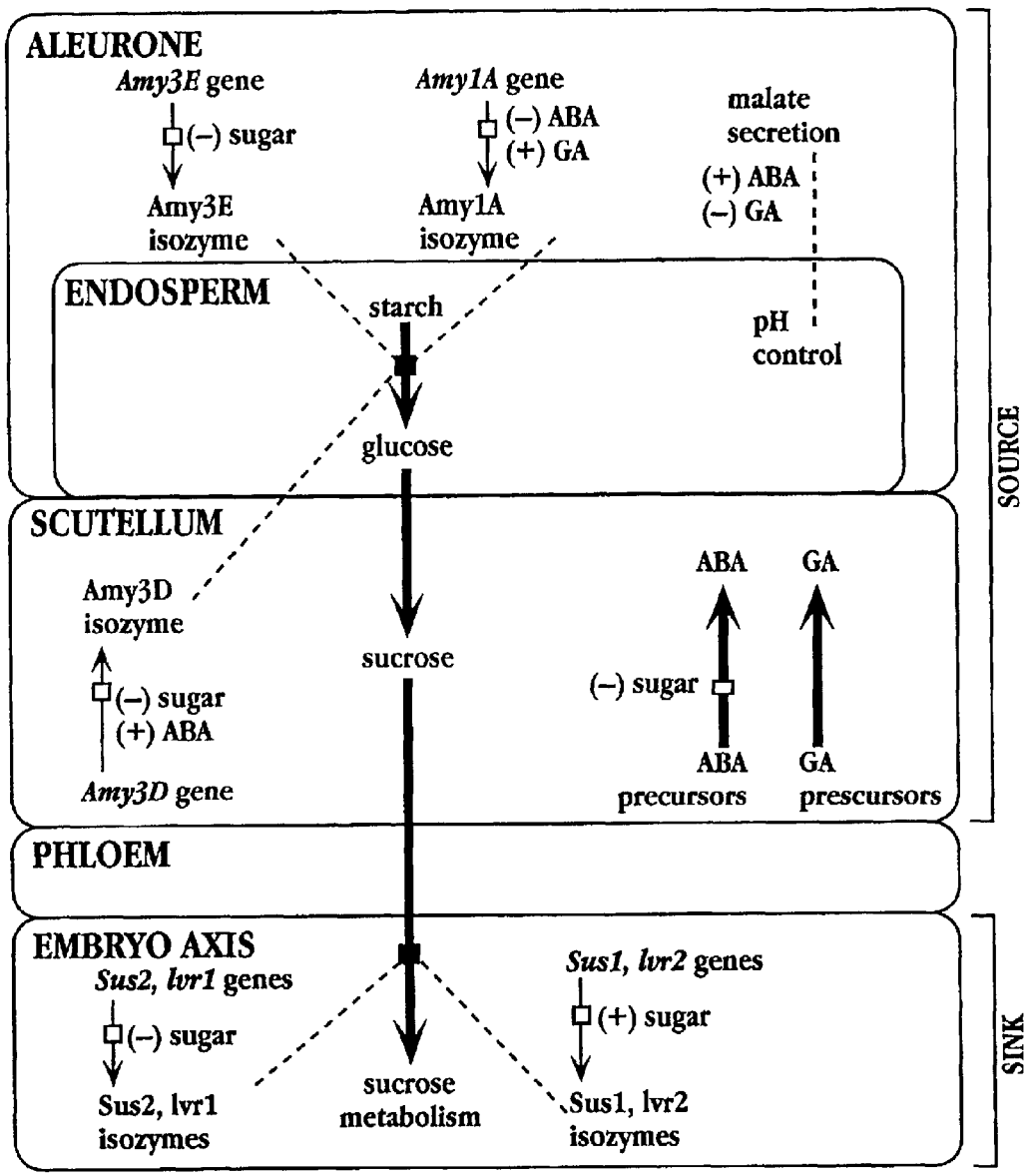
FIG. 1 shows metabolic signals and gibberellic acid (GA) signals in the regulation of cereal seed development.

The terms below have the following meaning, unless indicated otherwise in the specification.

"Cell culture" refers to cells and cell clusters, typically callus cells, growing on or suspended in a suitable growth medium.

"Germination" refers to the breaking of dormancy in a seed and the resumption of metabolic activity in the seed, including the production of enzymes effective to break down starches in the seed endosperm.

"Inducible" means a promoter that is upregulated by the presence or absence of a small molecule. It includes both indirect and direct inducement.

"Inducible during germination" refers to promoters which are substantially silent but not totally silent prior to germination but are turned on substantially (greater than 25%) during germination and development in the seed.

"Inducible by sugar depletion" or "inducible by sugar deprivation" refers to promoters which are substantially silent or operate at a relatively low level in the presence of sugars such as those defined below, but are upregulated substantially (greater than 25% increase in expression) in the absence of or in low levels of sugars, in either the germinating seed or in cell culture. In cell culture, the sugar depletion induction response level may be measured by comparing the difference in promoter activity when cells are cultured in the presence of 3% glucose vs. 0% glucose (or alternatively, 3% mannitol). Examples of promoters that are inducible by sugar depletion include promoters from the RAmy3D and RAmy3E rice α-amylase genes.

"Sugars", as used herein, refer to sugars that are capable of repressing or inhibiting the transcriptional activity of the RAmy3D promoter (and other sugar-repressible promoters), and include any monosaccharide or disaccharide that is capable of producing ATP by the glycolytic pathway via initial phosphorylation of the sugar. Examples include, but are not limited to, glucose, sucrose, maltose, fructose, or other phosphorylatable sugar. Sugar alcohols like mannitol, sorbitol, and glycerol, which are not capable of producing ATP via initial phosphorylation and entry into the glycolytic pathway, do not repress the transcriptional activity of the RAmy3D promoter, and are thus not considered "sugars" in the context of this invention.

"Small molecules", in the context of promoter induction, are typically small organic or bioorganic molecules less than about 1 kilodalton. Examples of such small molecules include sugars, sugar-derivatives (including phosphate derivatives), and plant hormones (such as, gibberellic or absissic acid).

"Specifically regulatable" refers to the ability of a small molecule to preferentially affect transcription from one promoter or group of promoters (e.g., the α-amylase gene family), as opposed to non-specific effects, such as, the enhancement or reduction of global transcription within the cell by, for example, increases or decreases in cell division, cell size, or metabolic rate.

A "transcription regulatory region" or "promoter" refers to nucleic acid sequences that influence and/or promote initiation of transcription. Promoters are typically considered to include regulatory regions, such as enhancer or inducer elements.

"Operably linked" refers to components of a chimeric gene or an expression cassette that function as a unit to express a heterologous protein. For example, a promoter operably linked to a heterologous DNA, which encodes a protein, promotes the production of functional mRNA corresponding to the heterologous DNA.

A "promoter element" refers to a plant or plant-virus promoter which is effective to express a coding sequence operatively linked the promoter under selected conditions in plant cells. A promoter element may be a native plant promoter, e.g., an gene promoter from monocots, or dicots, a plant-virus promoter, e.g., the 35S CMV promoter, or a hybrid plant or plant-virus promoter, that is, a promoter constructed of elements from various promoters. In some contexts, "promoter element" and "promoter" are used interchangeably.

A "sugar-regulatory sequence" or "sugar-depletion responsive sequence" is a sequence of nucleotides taken from the rice Amy3D promoter that has been discovered, in accordance with the invention, to confer ability of the promoter to upregulate promoter activity, e.g., expression of a gene operatively linked to the promoter, under conditions of sugar depletion or deprivation. The sugar-regulatory sequences include those defined by SEQ ID NOS: 1, 2, 3, 4 and combinations thereof.

"Sugar depletion" refers to utilization and depletion of existing sugar in plant cells or in the plant cell environment, by plant cell metabolism.

"Sugar deprivation" means that plant cells are grown in the absence of or at low concentrations of sugar.

A "heterologous sequence", in the context of a sugar-regulatory sequence, means a sugar-regulatory sequence that is placed in a promoter element (i) that normally does not contain such sequence, (ii) in duplicate copies in a promoter element that may or may not contain such a sequence in native form, and/or (iii) at promoter regions normally not containing the heterologous sequence.

A "homologous position", in the context of a promoter region, refers to a position in a plant promoter gene, preferably a monocot α-amylase gene, that corresponds to the position in a rice Amy3D gene, when the two promoters are aligned.

A plant promoter is aligned with the rice Amy3D promoter sequence when the two sequences are optimally aligned, meaning the alignment giving the highest % identity score between the sequences. Such alignment can be preformed using a variety of commercially available sequence analysis programs, such as the "GENEWORKS" program, or the local alignment program LALIGN with a ktup of 1, default parameters and the default PAM. A preferred alignment is the one performed by the CLUSTAL-W program from MacVector (TM), operated with an open gap penalty of 10.0, an extended gap penalty of 0.1, and a BLOSUM similarity matrix. If a gap needs to be inserted into a first sequence to optimally align it with a second sequence, the percent identity is calculated using only the residues that are paired with a corresponding amino acid residue (i.e., the calculation does not consider residues in the second sequences that are in the "gap" of the first sequence).

"Heterologous DNA" or "foreign DNA" refers to DNA which has been introduced into plant cells from another source, or which is from a plant source, including the same plant source, but which is under the control of a promoter or terminator that does not normally regulate expression of the heterologous DNA.

"Heterologousprotein" is a protein, including a polypeptide, encoded by a heterologous DNA.

A "product" encoded by a DNA molecule includes, for example, RNA molecules and polypeptides.

"Removal" in the context of a metabolite includes both physical removal as by washing and the depletion of the metabolite through the absorption and metabolizing of the metabolite by the cells.

"Substantially isolated" is used in several contexts and typically refers to the at least partial purification of a protein or polypeptide away from unrelated or contaminating components. Methods and procedures for the isolation or purification of proteins or polypeptides are known in the art.

"Stably transformed" as used herein refers to a cereal cell or plant that has foreign nucleic acid stably integrated into its genome which is transmitted through multiple generations.

A DNA sequence is "derived from" a gene, such as a rice or barley α-amylase gene, if it corresponds in sequence to a segment or region of that gene. Segments of genes which may be derived from a gene include the promoter region, the 5' untranslated region, and the 3' untranslated region of the gene.

II. Chimeric, Sugar-Depletion Inducible Promoters

The metabolic regulation signals and plant hormone signals that control cereal seedling development in rice are diagrammed in FIG. 1. As seen, synthesis of the rice α-amylase protein Amy3E is stimulated by sugar depletion in the seed aleurone cells, and Amy1A α-amylase production is stimulated by the plant hormone gibberellic acid (GA). In the scutellum layer, sugar depletion induces synthesis of the Amy3D α-amylase. The α-amylases are secreted into the endosperm of the seed, resulting in conversion of starch to sugar, which in turn represses Amy3D and Amy3E synthesis. The sucrose produced is made available to the embryo for embryo growth.

A similar response is observed in rice cell culture. Amy3D is expressed when the cells are deprived of metabolizable sugars (i.e., grown in the absence of metabolizable sugars such as glucose, sucrose, maltose, fructose, galactose) or in response to sugar depletion in the growth medium. The converse is also true. When sugar concentrations are elevated in rice cell culture, Amy3D expression is reduced (Rodriguez, R., WO 95/14099; Yu S -M, et al. (1991) J. Biol. Chem. 266:21131–21137).

A. Sugar-Depletion Responsive Sequences

By deletion and site-directed mutation analyses described below and in the Examples, Amy3D promoter sequence elements responsive to sugar depletion have been defined.

Figure 2A:
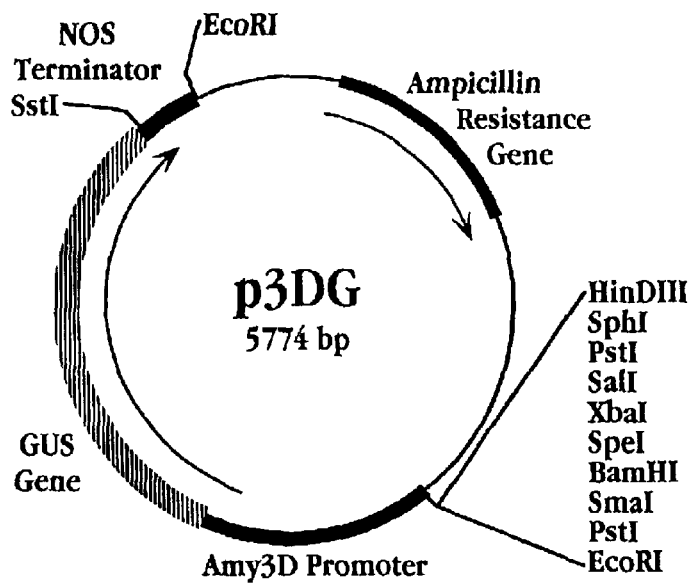
FIG. 2A shows the p3DG expression plasmid for testing expression of various deletions and site-specific mutations in regions of the RAmy3D promoter operably linked to the structural gene for β-glucuronidase(GUS)
Figure 2B:
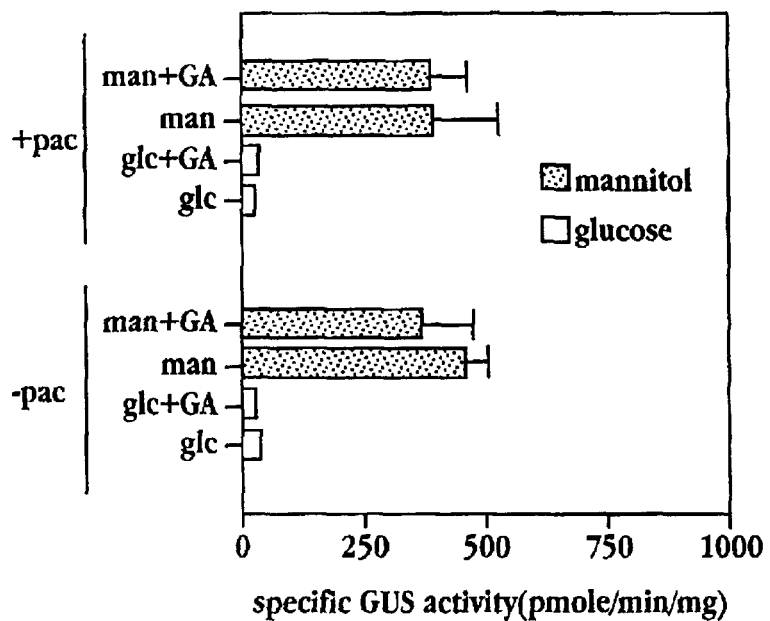
FIG. 2B shows that glucose (glc) treatment reduces expression, while mannitol (man) treatment (sugar depletion) does not affect expression from the RAmy3D promoter, as indicated by GUS activity in rice cell lines transformed with the RAmy3D/GUS expression plasmid of FIG. 2A.

The ability of sugar depletion to upregulate Amy3D expression is demonstrated in FIGS. 2A and 2B. FIG. 2A shows a plant transformation vector, designated p3DG, designed for transformation of monocots, containing the GUS gene under the control of the RAmy3D promoter (Example 1B). The plasmid p3DG contains 876 bp of RAmy3D 5' flanking region plus 66 bp of the 5' untranslated leader sequence linked to the GUS coding region (FIG. 2A). The GUS gene encodes the enzyme beta-glucuronidase that produces a blue chromophore in tissues expressing the gene.

Rice plant cells were transformed with the vector according to standard methods, such as detailed in PCT application WO 95/14099, which is incorporated herein by reference, and is described in Example 1C. Successful transformants were then grown in suspension culture under sugar-depletion vs. glucose treatment conditions, both in the presence and absence of GA. Mannitol is a non-metabolizable sugar alcohol which does not interact with the RAmy3D promoter, and is used in sugar-depletion experiments to provide an osmotic strength equivalent to that of the glucose treatment experiments. FIG. 2B shows the levels of GUS expression observed, shown as GUS activity (pmole/min/mg tissue). GUS expression in transformed cells cultured under sugar-depletion conditions (i.e. in the presence of mannitol), either +/−GA, was at least 10–15 times higher than in cells cultured in glucose-containing media.

The 5' DNA region between nucleotides −876 to +66 (where +1 is the site of initiation of transcription) of the Amy3D promoter contains all of the regulatory sequences necessary for metabolic regulation of Amy3D transcription. In a series of deletions proceeding from the 5' end of the Amy3D promoter, diagrammed in FIG. 3A, the first sharp decline in sugar depletion-induced GUS expression in the transformed cell lines occurred upon deletion of the region between nucleotides −206 and −98 (FIG. 3B, Example 1E.1), indicating that this region contains sequences critical for high-level expression of the Amy3D promoter under sugar depletion conditions.

Figure 4A:
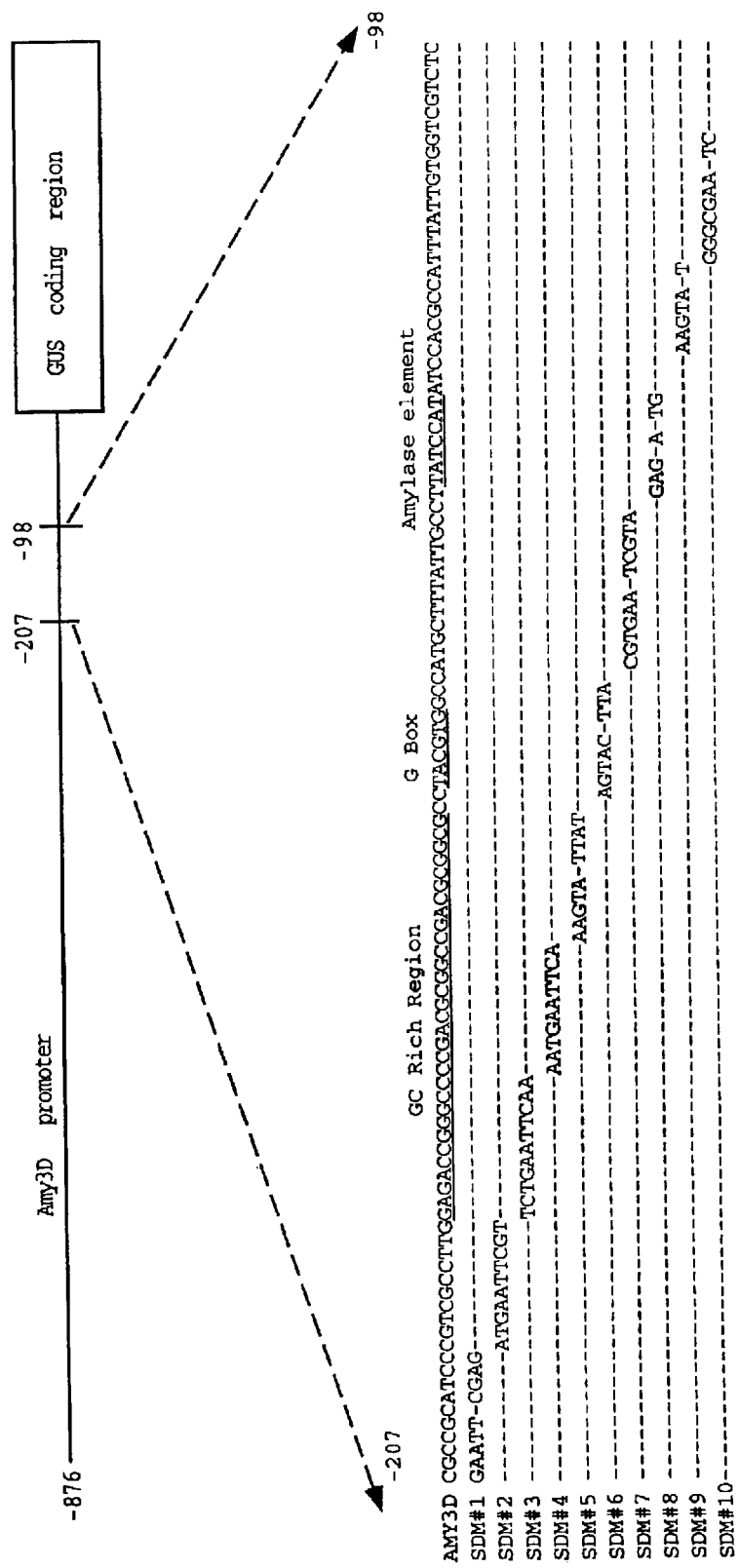
FIG. 4A shows the RAmy3D promoter in the region between nucleotides −207 and −98 and site-directed mutations of the promoter where nucleotides matching the native promoter are indicated with (−), the native promoter in the −207 to −98 region having the sequence SEQ ID NO:6 and the mutated promoter regions SDM#1 through SDM#10 having the sequences SEQ ID NO:7 through SEQ ID NO:16, respectively.
Figure 4B:
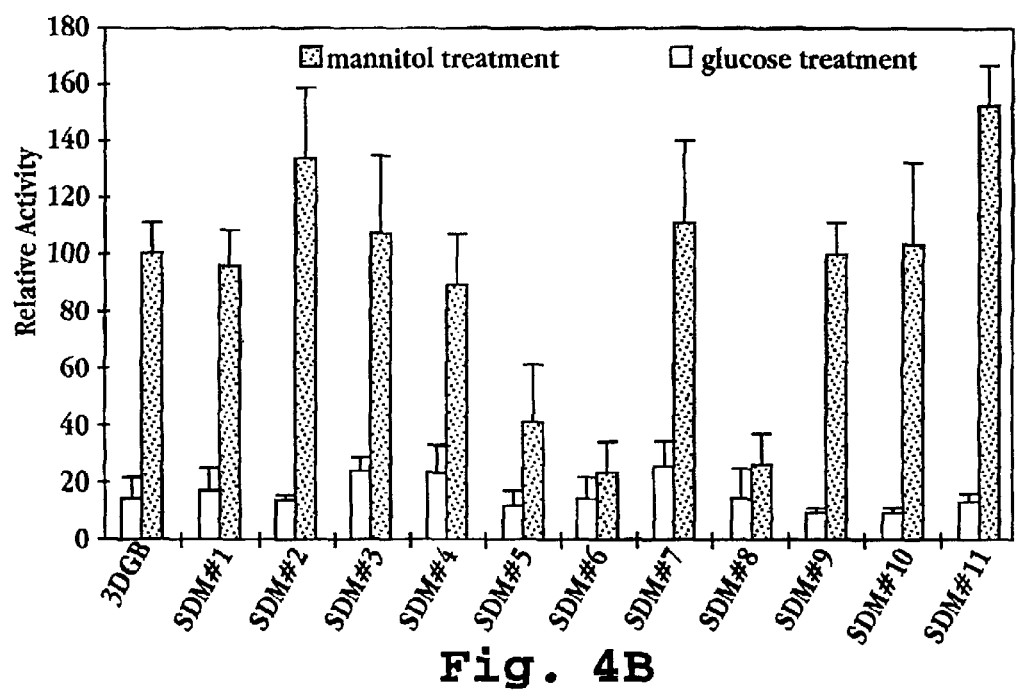
FIG. 4B shows levels of transient GUS expression observed in mannitol-treated (dark bars) and glucose-treated (light bars) rice protoplasts transformed with expression plasmids containing the mutations shown in FIG. 4A.

This region was examined in greater detail using full-length Amy3D promoters containing the short mutated segments shown in FIG. 4A. Levels of GUS expression in a transient expression system (Example 1D) as a function of mutated promoter segment were measured, with results presented in FIG. 4B and Example 1E.2.

The promoter sequences critical for sugar-depletion response in the Amy3D promoter were localized to the region having the sequence identified herein as SEQ ID NO:1, which extends between nucleotides −166 and −125 of the Amy3D gene. In particular, three critical sequences have been identified: a) between nucleotides −166 and −157 and identified as SEQ ID NO:2; b) between nucleotides −155 and −147 and identified as SEQ ID NO:3; and c) between nucleotides −132 and −125 and identified herein as SEQ ID NO:4.

The Amy3D sequence(s) critical for upregulation under sugar-depletion conditions (SEQ ID NOS:1–4 and combinations thereof) may be used to introduce sugar-depletion regulation into plant promoters not naturally regulated by sugar concentration, and to enhance or modulate the sugar-depletion response, e.g., by introducing multiple copies of the sequence into a plant promoter, for example a plant α-amylase gene promoter.

Combinations of these elements, such as the sequence between nucleotides −166 and −147 and identified herein as SEQ ID NO:5, are also contemplated. Also contemplated are sugar-depletion response sequences that are identical to the sequences disclosed herein, as well as sequence elements which contain a small number of point mutations, deletions, or insertions, which do not compromise the induction of expression under sugar-depletion conditions.

B. Chimeric Promoters

The invention includes, in one aspect, a chimeric promoter containing one or more of the sugar-depletion responsive sequences identified above. The promoter is designed for upregulating expression of a coding sequence operatively linked to the promoter, under conditions of sugar depletion or deprivation in a plant cell. The promoter includes (i) a promoter element effective to express the coding sequence in plant cells, under selected conditions, and (ii) carried in said promoter element, one or more or the above heterologous sugar-depletion regulatory sequences identified as SEQ ID NO:1, SEQ ID NO: 2, SEQ ID NO:3, SEQ ID NO:4, and combinations thereof.

Various embodiments of the chimeric promoter are described below, with reference to methods of preparing such promoters. These methods are also described in the context of another aspect of the invention: a method of enhancing the sugar-depletion response of a plant or plant-virus promoter, by introducing one or more of the sugar-depletion regulatory sequences into the promoter element.

The method is effective to increase the sugar-depletion induction level of the chimeric promoter at least 2-fold over the sugar-depletion induction level of the unmodified gene promoter.

Suitable promoters include those that transcribe the cereal α-amylase genes and are induced by small molecules, including phytohormones such as gibberellic acid or absissic acid, or by sugar depletion. Representative promoters include the promoters from the rice α-amylase RAmy1A, RAmy1B, RAmy2A, RAmy3A, RAmy3B, RAmy3C, RAmy3D, and RAmy3E genes, and from the pM/C, gKAmy141, gKAmy155, Amy32b, and HV18 barley α-amylase genes. Such promoters, and their method of selection are detailed in above-cited PCT application WO 95/14099.

Other suitable plant promoters include monocot and dicot plant promoters, including, but not limited to, the actin, ubiquitin, Adh, Em, Lea, glutellin, hordein, zein, and Rubisco promoters. Also contemplatedare plant-viruspromoters, such as the 35S CMV promoter.

The sugar-depletion responsive sequence of the present invention may be substituted for regulatory sequences in the promoters of other plant genes, such as plant α-amylase genes. For example, a sugar-depletion responsive sequence of the present invention may be substituted for the GA responsive element (GARE), or the abscisic acid responsive element (ABRE), in promoters which are induced by GA or abscisic acid, respectively, converting these promoters from phytohormone-regulated promoters to metabolically-regulated(i.e., sugar-depletion regulated) promoters.

Alternatively, or in addition, sugar-depletion responsive elements may also be substituted into structurally similar regions of other plant promoters, including but not limited to monocot α-amylase promoters. By aligning the sequences of the sugar-depletion responsive sequences with the sequence of the target promoter, regions in the target promoter which are homologous to the sugar depletion-responsive element may be identified. Such alignments may be performed using any of a number of readily-available sequence alignment programs, including the CLUSTAL W program (MacVector (TM); Oxford Molecular, Oxford, UK). Promoters contemplated include, but are not limited to, the GA-inducible RAmy1A, Amy32b, and HV18 promoters.

Alternatively, one or more sugar-depletion responsive elements of the present invention may be introduced into non-essential region(s) of a plant promoter. The non-essential regions of these promoters may be identified using the experimental methods detailed herein, e.g., locating sequence regions of the promoter which, when mutated, show promoter activity substantially similar to that of the wildtype promoter.

In another embodiment, the sugar-depletion responsive sequences of the present invention may be introduced into promotors which in their native form are upregulated by sugar depletion, to further enhance the sugar-depletion induction response of these promoters. Such promoters include the rice α-amylase RAmy3D and RAmy3E promoters. For example, it is contemplated that the presence of multiple copies of the sugar-depletion responsive sequences will enhance the sugar depletion induction response of the RAmy3D or RAmy3E promoters.

III. Chimeric Gene

In another aspect, the invention includes a vector for use in transforming a monocotyledenous plant. The vector comprises a chimeric gene having, operatively linked in sequence in a 5' to 3' direction, (i) a chimeric promoter as described above, (ii) operatively linked to the chimeric promoter, a gene encoding a protein to be expressed, and (iii) a 3' untranslated terminator region.

A. Chimeric Promoter

Chimeric promoters are described above. In one embodiment, where the gene is employed in protein production in a monocot cell culture, preferred promoters are chimeric RAmy3E and RAmy3D gene promoters described above. In another embodiment, where the gene is employed in protein production in germinating seeds, a preferred promoter is a chimeric RAmy1A gene promoter containing one or more sugar-depletion responsive elements described above, to permit regulation control by both gibberellic acid and sugar concentration during seed germination.

B. Expressed Protein Gene

The gene encoding the protein to be expressed may include a) the monocot α-amylase gene which is under the control of the native promoter from which the improved promoter is derived; b) a gene encoding a monocot α-amylase normally controlled by a different promoter, or a gene encoding a monocot protein other than α-amylase; or c) a gene encoding a protein from a source other than a monocot plant. The proteins of categories b) and c) are collectively referred to as heterologous proteins.

The expressed protein, if other than a monocot α-amylase, may include a fusion of an N-terminal region corresponding to a portion of a monocot α-amylase signal sequence peptide and, immediately adjacent to the C-terminal amino acid of said portion, the protein. Suitable monocot α-amylase signal sequence peptides include, but are not limited to, those described in PCT publication WO 95/14099, incorporated by reference herein.

The expressed protein, with or without adjacent signal sequence, may include therapeutic proteins such as factor VIII or α1-antitrypsin (AAT); vaccines; industrial enzymes such as subtilisin; and proteins and peptides of nutritional importance. The nucleic acid coding sequence for these proteins are available from a variety of reference and sequence database sources. The coding sequence in a fusion protein gene is constructed such that the final codon in the signal sequence is immediately followed by the codon for the N-terminal amino acid of the mature form of the protein to be expressed. The coding sequence for a heterologous protein may be codon-optimized for optimal expression in plant cells.

C. 3' Untranslated Region

The gene also includes, downstream of the coding sequence, the 3' untranslated region (3' UTR) from an inducible monocot gene, such as one of the monocot α-amylase genes listed above. The transcriptional termination region may be selected, particularly for stability of the mRNA to enhance expression. Polyadenylation tails, Alber and Kawasaki, *Mol. and Appl. Genet.* 1:419–434 (1982) are also commonly added to the expression cassette to optimize high levels of transcription and proper transcription termination, respectively. Polyadenylation sequences include but are not limited to the *Agrobacterium* octopine synthetase signal, Gielen, et al., *EMBO J.* 3:835–846 (1984) or the nopaline synthase of the same species Depicker, et al., *Mol. Appl. Genet.* 1:561–573 (1982).

IV. Plant Transformation

For transformation of plants, the chimeric gene comprising the chimeric promoter of the present invention, a gene encoding a protein to be expressed, and a 3' untranslated terminator region, is placed in a suitable expression vector designed for operation in plants. The vector includes suitable elements of plasmid or viral origin that provide necessary characteristics to the vector to permit the vectors to move DNA from bacteria to the desired plant host. Suitable transformation vectors are described in related application PCT WO 95/14099, published May 25, 1995, which is incorporated by reference herein.

A. Transformation Vector

Vectors containing the improved promoter of the present invention may also include selectable markers for use in plant cells, such as the nptII or hph genes, for selection in kanamycin- or hygromycin-containingmedia, respectively, or the phosphinothricinacetyltransferasegene, for selection in medium containing phosphinothricin (PPT).

The vectors may also include sequences that allow their selection and propagation in a secondary host, such as sequences containing an origin of replication and a selectable marker such as antibiotic or herbicide resistance genes, e.g., HPH (Hagio et al., *Plant Cell Reports* 14:329 (1995) and van der Elzer, *Plant Mol Biol.* 5:299–302 (1985). Typical secondary hosts include bacteria and yeast. In one embodiment, the secondary host is *Escherichia coli,* the origin of replication is a colE1-type, and the selectable marker is a gene encoding ampicillin resistance. Such sequences are well known in the art and are commercially available as well (e.g., Clontech, Palo Alto, Calif.; Stratagene, La Jolla, Calif.).

The vectors which contain the chimeric promoter of the present invention may also be modified to intermediate plant transformation plasmids that contain a region of homology to an *Agrobacterium tumefaciens* vector, a T-DNA border region from *Agrobacterium tumefaciens,* and chimeric genes or expression cassettes (described above). Further, the vectors of the invention may comprise a disarmed plant tumor inducing plasmid of *Agrobacterium tumefaciens.*

B. Transformation of Plant Cells

The plants used in the process of the present invention are derived from monocots, particularly the members of the taxonomic family known as the Gramineae. This family includes all members of the grass family of which the edible varieties are known as cereals. The cereals include a wide variety of species such as wheat (*Triticum sps.*), rice (*Oryza sps.*) barley (*Hordeum sps.*) oats, (*Avena sps.*) rye (*Secale sps.*), corn (*Zea sps.*) and millet (*Pennisettum sps.*). In the present invention, preferred family members are rice and barley.

Plant cells or tissues derived from the members of the family are transformed with expression constructs (i.e., plasmid DNA into which the chimeric gene of the invention has been inserted) using a variety of standard techniques (e.g., electroporation, protoplast fusion, *Agrobacterium* infection, or microparticle bombardment). In the present invention, particle bombardment is the preferred transformation procedure.

Various methods for direct or vectored transformation of plant cells, e.g., plant protoplast cells, have been described, e.g., in above-cited PCT application WO 95/14099. As noted in that reference, promoters directing expression of selectable markers used for plant transformation (e.g., nptII) should operate effectively in plant hosts. One such promoter is the nos promoter from native Ti plasmids, Herrera-Estrella, et al., *Nature* 303:209–213 (1983). Others include the 35S and 19S promoters of cauliflower mosaic virus, Odell, et al, *Nature* 313:810–812 (1985), and the 2' promoter, Velten, et al., *EMBO J.* 3:2723–2730 (1984).

In one preferred embodiment, the embryo and endosperm of mature seeds are removed to exposed scutellum tissue cells. After propagating scutellar tissue into callus, the callus cells may be transformed by DNA bombardment or injection, or by vectored transformation, e.g., by *Agrobacterium* infection after bombarding the scutellar cells with microparticles to make them susceptible to *Agrobacterium* infection (Bidney et al., *Plant Mol Biol.* 18:301–313 (1992)).

One preferred transformation follows the methods detailed generally in Sivamani, E. et al., *Plant Cell Reports* 15:465 (1996); Zhang, S., et al., *Plant Cell Reports* 15:465 (1996); and Li, L., et al., *Plant Cell Reports* 12:250 (1993).

V. Cell Culture Production of Expressed Protein

In another aspect, the invention relates to expression of recombinant proteins in cereal cell culture, the expression regulated by the chimeric promoter of the present invention. In one embodiment of the invention, the cells are derived from scutellar epithelium of cereal plants. Example 1A outlines a preferred method for initiation of scutellar callus and suspension cultures. The chimeric promoters, vectors and methods described above may be implemented in the practice of this aspect of the invention.

Transgenic plant cells which express the recombinant protein under the control of the chimeric promoter of the present invention are cultured under conditions that favor plant cell growth, until the cells reach a desired cell density, then under conditions that favor expression of the protein under the control of the chimeric promoter.

For example, rice cells transformed with an expression vector of the type described above containing the sequence encoding human α1-antitrypsin (AAT) fused to the coding sequence for the Amy3D signal sequence, under the control of a chimeric Amy3D promoter, are grown in shake flasks (or in a bioreactor) using AA2 growth media containing 3% sucrose (AA2+sucrose). Cells are cultured at 28° C. in the dark with constant shaking for aeration. The medium is replenished every five days to maintain healthy cell growth. The pH of the media is maintained at pH 5.7. Since the AAT coding sequence is under the control of a sugar-depletion responsive promoter (chimeric Amy3D), recombinant AAT production is induced by diluting or changing the media to sucrose-free media (AA2-sucrose). Upon induction, recombinant AAT is expressed in the cells and secreted into the culture medium by virtue of the Amy3D signal peptide. Recombinant AAT is isolated from the culture medium and purified to homogeneity using standard techniques known to those of skill in the art.

VI. Production of Expressed Protein in Germinating Seeds

In this embodiment, monocot cells transformed as above are used to regenerate plants, seeds from the plants are harvested and then germinated, and the mature protein is isolated from the germinated seeds.

Plant regeneration from cultured protoplasts or callus tissue is carried by standard methods, e.g., as described in Evans et al., *HANDBOOK OF PLANT CELL CULTURES* Vol. 1: (MacMillan Publishing Co. New York, 1983); and Vasil I. R. (ed.), *CELL CULTURE AND SOMATIC CELL GENETICS OF PLANTS,* Acad. Press, Orlando, Vol. 1, 1984, and Vol. 111, 1986, and as described in the above-cited PCT application.

The transgenic seeds obtained from the regenerated plants are harvested, and prepared for germination by an initial stepping step, followed by malting as detailed, for example, in above-identified PCT application WO 95/14099.

The mature protein secreted from aleurone cells into the endosperm tissue of the seed can be isolated by standard methods. Typically, the seeds are mashed to disrupt tissues, the seed mash is suspended in a protein extraction buffer, and the protein is isolated from the buffer by conventional means.

Stably transformed transgenic cereal seeds prepared as described above may also be used as a source of homogenous populations of callus cells, which can be cultured to produce the recombinant protein in cell culture.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

The following examples are provided by way of illustration only and not by way of limitation. Those of skill will readily recognize a variety of noncritical parameters which could be changed or modified to yield essentially similar results.

EXAMPLES

General Methods

Generally, the nomenclature and laboratory procedures with respect to standard recombinant DNA technology can be found in Sambrook, et al., *Molecular Cloning—A Laboratory Manual*, Cold Spring Harbor Laboratory, Cold Spring Harbor, N.Y. 1989 and in S. B. Gelvin and R. A. Schilperoot, *Plant Molecular Biology*, 1988. Other general references are provided throughout this document. The procedures therein are known in the art and are provided for the convenience of the reader.

Example 1

Expression of β-glucuronidase Under the Control of the α-amylase Promoter in Rice Cell Culture A. Initiation of Scutellar Callus and Suspension Cultures.

Rice seeds (*Oryza sativa* L. cv. M202) were provided by Dr. M. Brandon (California Rice Experimental Station). Seeds were dehulled, washed three times with water, rinsed in 70% ethanol for 20 sec and then surface-sterilized in 1% sodium hypochlorite with a few drops of Tween 20 under vacuum for 20 min. Sterilized seeds were washed three times with sterile distilled water. Seven seeds were placed in 15 cm petri dishes containing LS medium with 2 mg/l 2,4-D and 30 g/l sucrose. The seeds were incubated in the dark at 28° C. and checked periodically to monitor the growth of scutellar-derived callus. Callus formation from scutellum tissue and/or embryo was visible after 5 days. After 30 to 40 days, clumps of friable calli, about 1 cm in diameter, were saved and the remaining tissue was discarded.

To initiate a suspension culture, friable calli were gently agitated in a petri dish with liquid AA medium as described by Thompson J A, Abdullah R and Cocking E C, Protoplast culture of rice (*Oryza sativa* L.) using media solidified with agarose (Plant Sci. (1986) 47:123–133) to reduce the calli to small clusters of cells. Cell clusters from about 20–30 clumps of calli were then transferred to a 125 ml Erlenmeyer flask and the liquid was replaced with 25 ml of fresh AA medium. The flasks were incubated in the dark on a rotary platform shaker at 110 rpm and 28° C. The primary culture was sub-cultured every 4 to 5 days with repeated screening for small cell clusters. This was accomplished by passing the culture sequentially through nylon filters of 1000 µm and 500 µm pore size. After two months of subculture, a finely divided and rapidly growing suspension culture was obtained. This culture was subsequently maintained by weekly subculture in AA medium containing 3% sucrose.

B. Construction of RAmy3D/GUS Gene Fusion Plasmids

The RAmy3D promoter/GUS gene fusion expression plasmid shown in FIG. 2A was constructed in three steps. First, a 1.5 kb SalI fragment containing the promoter and part of the coding region from rice genomic clone λOSg1A as described by Huang, et al., (1990; Nucleic Acid Res., 18:7007–7014) was subcloned into pBluescript KS-to produce the plasmid p1AS1.5. The AluI fragment from p1AS1.5 containing 876 bp of promoter and 66 bp of 5' untranslated region was subcloned into the EcoRV site of "pBLUE-SCRIPT KS+" to form p1Alu.

Second, a plasmid containing a promoterless GUS cassette was constructed by subcloning the HindIII/EcoRI GUS cassette from pB1101 (Jefferson R A, (1987a) Plant Mol. Biol. Reporter, 5:387–405) into pUC19 to form pB1201. A pUC19 polylinker in front of the GUS coding region provides convenient cloning sites for inserting promoter fragments. Third, the RAmy3D promoter fragment was inserted into the promoterless GUS plasmid to produce the plasmid p3DG. The XbaI/AluI (in HindIII site) promoter fragment from p1Alu was ligated into XbaI/SmaI digested pB1201. The final 11 bp of RAmy3D 5' untranslated region was substituted by 21 bp from the polylinker resulting in the 5.83 kb plasmid, p3DG.

The junction between the RAmy3D promoter and the 5' end of the GUS gene was confirmed by DNA sequencing. DNA restriction digest, DNA gel electrophoresis, ligation, transformation, plasmid DNA isolation and DNA sequencing followed standard procedures (Sambrook, et al., (1989) supra).

To prepare 5' deletions of the RAmy3D promoter, plasmid pDG3 was digested with PstI and XbaI for constructing a 5' unidirectional deletion series using the Bluescript Exo/Ming DNA Sequencing System (Stratagene). The deletion endpoints were located by DNA sequencing using the dideoxy method, The predicted transcription start site of the RAmy3D gene was used as the reference point for identifying locations within the promoter sequence.

Mutations were introduced into specific regions of the RAmy3D promoter in p3DG using standard oligonucleotide-directed in vitro mutagenesis methods. To facilitate screening of putative mutants, restriction endonuclease sites were included in the mutagenic sequences. All site-directed mutations (SDM) were confirmed by sequencing using the dideoxy method (Amersham Life Sciences).

Plasmid p3DGB, which was prepared by inserting a bar gene cassette into p3DG, was the vector used in the transient expression experiments. A NotI fragment containing 35S promoter/bar coding region/Nos 3' region was cut from pBARGUS (Fromm, M. E. (1990) Bio/Technology 8:833–839), blunted with T4 DNA polymerase and inserted into the SmaI site of pBluescript SK(-) to make pBSB. The bar gene cassette was then cut out of pBSB by double digestion with XbaI and HindIII and inserted into similarly digested pUC19 to form pUCB. The bar gene cassette was then cut from pUBC as an EcoRI fragment and ligated into the EcoRI site of p3DG and each of the site-directed Amy3D mutant constructs for transient expression analysis.

C. Preparation of Transgenic Rice Cell Lines and Analysis of Amy3D/GUS Gene Expression Plasmids were transformed into rice cells by microprojectile bombardment using the Biolistic PDS-1000/He (BioRad Laboratories) with 9 MPa (1300 psi) rupture disks. Suspension culture cells for bombardment were layered 1–2 mm thick on sterile filter paper disks on AA2 agar medium(ref 52) and were incubated in the dark at 28° C. for 5 days.

Target cells were cotransformed by gold particles of 1 µm in diameter coated with 2.5 µg of pMON410 (containing the hph gene driven by the CaMV 35S promoter; Rogers S. G. et al. (1987) Meth. Enzymol. 153:253–277) and 2.5 µg of the desired promoter/GUS plasmid (for 6 bombardments).

Plates to be bombarded were placed 8 cm below the stopping plate under vacuum at 95 kPa (28 in. Hg). The bombarded cells were incubated in the dark at 28° C. for 5 days without selection pressure and transferred to AA2 agar medium containing 30 mg/l hygromycin B. After 2 weeks, cells were transferred to medium containing 50 mg/l hygromycin B. Transfer of cells to fresh AA2 medium containing 50 mg/l hygromycin B was done every 2 weeks until hygromycin-resistant calli reached 1 cm in diameter.

Transgenic callus clones containing the promoter/GUS fusion constructs were identified by GUS histochemical assay (Jefferson, R. A. et al. (1987b) EMBO J. 6:3901–3907) or by PCR amplification of template DNA from the transgenic callus using forward and reverse primers which anneal to the 5' untranslated region of the Amy3D gene and to the GUS coding region, respectively.

Transgenic suspension cells were washed in two changes of basal medium plus 330 mM mannitol. Washed cells were then incubated in basal medium plus various chemicals for 2 days at 110 rpm on a rotary shaker at 28° C. GUS enzyme was extracted from the cells and assayed by the fluoromteric method (Jefferson et al. (1987b), supra) except that the cells were disrupted by sonication for 3 min at 50% duty cycle and 10 microtip limit on the Branson Sonifier 450. Transgenic cell lines containing the promoterless construct (RAmy3D promoter deleted to +40) were used as a negative control to define background levels of GUS activity.

D. Protoplast Isolation and Transient Expression Assays

Protoplast methods were modified from Lee et al. (*Planta* 178:325–333 (1989)). After removing AA2 medium, 7-day old suspension cells of rice cv. M202 were incubated with 40 ml of cell wall degrading enzyme solution (0.5% Onozuka Cellulase RS, 0.5% Macerozyme R-10; Yakult Honsha Co.), 5 mM MES, 0.32 M mannitol, 0.08 M glucose with CPW salts) overnight with 50 rpm shaking at 28° C. in the dark.

Digested cells were filtered through a 149 μm nylon filter and then through a 20 μm nylon filter, the filtrate was centrifuged for 12 min at 800 rpm, and gently resuspended in the same volume of CPW salts solution with 0.4M mannitol, pH 5.8.

Protplasts were centrifuged at 800 rmp for 7 min and resuspended in ASP buffer (70 mM aspartic acid monopotassium salt, 5 mM calcium gluconate, 5 mM MES and 0.4 M mannitol, pH 5.8) at a concentration of 10 million protoplasts/ml.

A 0.8 ml volume of protoplasts were mixed with 50 μg of p3DGB (or site-directed mutants of RAmy3D in p3DGB), 50 μg of pMef plasmid DNA (carrying the CaMV 35S promoter/luciferase gene fusion; Li et al. (1993) Plant Cell Rep. 12:250–255) and incubated on ice. After 30 min, protoplasts were transferred to an electroporation cuvette (0.4 cm electrode gap) and electroporated with a "GENE PULSER" electroporator (Bio-Rad) at 600 volt/cm, 500 μF, time constant 50 ms.

After incubation on ice for an additional 30 min, the protoplasts were transferred to room temperature for 30 min. The ASP buffer was removed by centrifugation. Protoplasts were resuspended in Kao and Michayluk Medium (Kao KN (1977) Mol. Gen. Genet. 150:225–230; Sigma Chemical Corp.) modified by removal of sugars, casamino acids and coconut water. For sugar-depletion experiments, 0.4 M mannitol was added to this medium, and for glucose treatments, 0.08 M glucose plus 0.32 M mannitol was added. Protoplasts were incubated for 2 days at 28° C. in the dark without shaking. After incubation, the protoplasts were harvested by centrifuging at 800 rpm for 5 min. After removing the supernatant, 100 μl of GUS/LUX extraction buffer (0.1 M potassium phosphate monobasic, 1 mM EDTA and 7 mM 2-mercaptoethanol) was added and cells were sonicated for 3 min at 10% duty cycle and 10 microtip limit settings on the Branson Sonifier 450. Sonicated protoplasts were centrifuged at 14,000 rpm for 5 min. The supernatant was used to measure the GUS and LUX activities (Bronstein, I. et al.(1994) Biotechniques 17:172–178; deWet J. R. et al.(1987) Mol. Cell Biol. 7:725–737).

E. Identification of Sugar-Depletion Responsive Elements

E1. Deletion Analysis

Figure 3A:
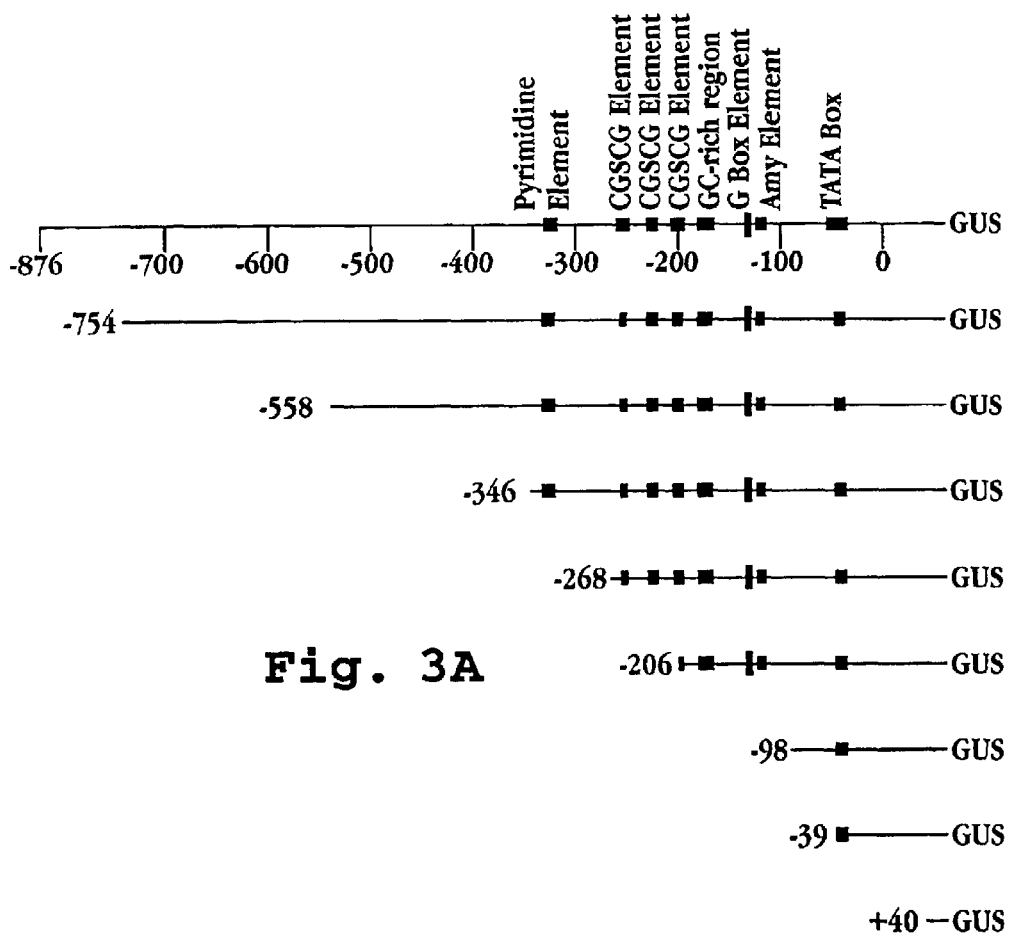
FIG. 3A shows a series of 5' deletion constructs of the RAmy3D promoter incorporated into the GUS expression plasmid.
Figure 3B:
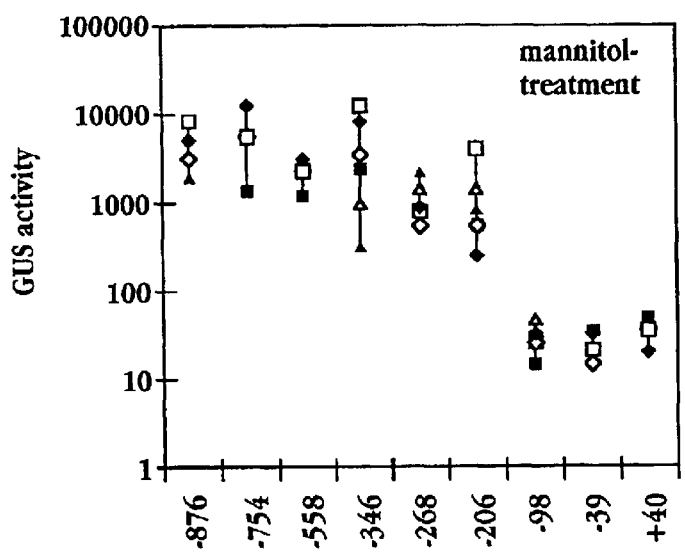
FIG. 3B shows levels of GUS expression observed in mannitol-treated transformed cell lines containing each of the series of RAmy3D deletions.

GUS expression in transformed rice cell lines was examined using plasmid constructs having the series of nested deletions in the Amy3D promoter shown in FIG. 3A. The uppermost three promoter deletions shown in the figure (−754, −558, and −346) all contain the identified promoter consensus regions: pyrimidine element; three CGSCG elements; the GC-rich element; the G box; the Amy element; and the TATA box. These three deletion constructs gave levels of GUS expression under sugar-depletion conditions (e.g., in the presence of 0.4 M mannitol) essentially equivalent to that level of expression seen under the same conditions with the full-length promoter (−876; FIG. 3B).

In the series of deletions proceeding from the 5' end of the Amy3D promoter, as diagrammed in FIG. 3A, the first sharp decline in sugar depletion-induced GUS expression occurred upon deletion of the region between nucleotides −206 and −98 (FIG. 3B), indicating that this region contains sequence critical for the sugar-depletion response of the promoter.

E2. Mutation Analysis

The −207 to −98 region was examined in greater detail using full-length Amy3D promoters containing short mutated segments SDM1-SDM10 as shown in FIG. 4A. Levels of GUS expression, as a function of mutated promoter segment, were measured in the transient expression assay system and the results shown in FIG. 4B. Levels of sugar-depletion induction comparable to that of the wild-type 3RAmy3D promoter were seen for all of the mutated segments except those labeled SDM5, SDM6, and SDM8. These three segments reside between nucleotides −166 and −125 of the Amy3D promoter, which has the sequence CGACG CGGCG CCTAC GTGGC CATGC TTTAT TGCCT TATCC AT identified herein as SEQ ID NO:1. The three segments are identified as: a) SDM5, having the sequence CGACGCGGCG extending between −166 and −157, identified as SEQ ID NO:2; b) SDM6, having the sequence CTACGTGGC extending between −155 and −147, and identified herein as SEQ ID NO:3; and c) SDM8, having the sequence TTATCCAT extending between −132 and −125 and identified herein as SEQ ID NO:4.

Figure 5A:
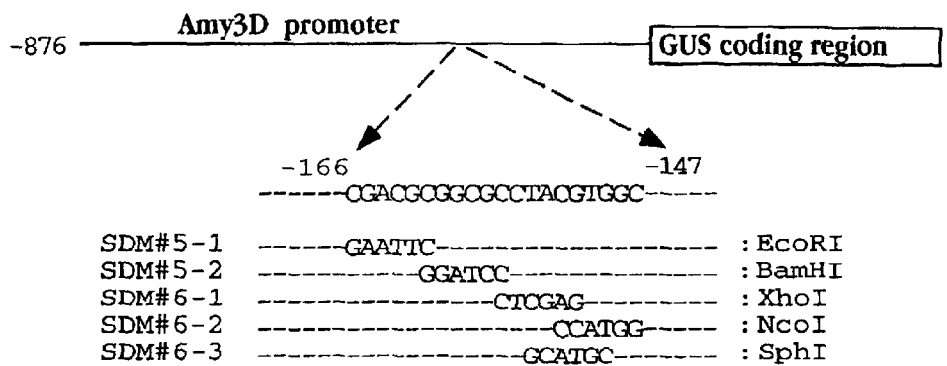
FIG. 5A shows the RAmy3D promoter in the region between nucleotides −166 and −147 identified as a sugar-responsive region of the promoter, and site-directed mutations within the region, the native promoter in that region having the sequence SEQ ID NO:5 and the mutated regions having the sequence SEQ ID NO:17 (SDM#5-1), SEQ ID NO:18 (SDM#5-2), SEQ ID NO:19 (SDM#6-1), SEQ ID NO:20 (SDM#6-2) and SEQ ID NO:21 (SDM#6-3)
Figure 5B:
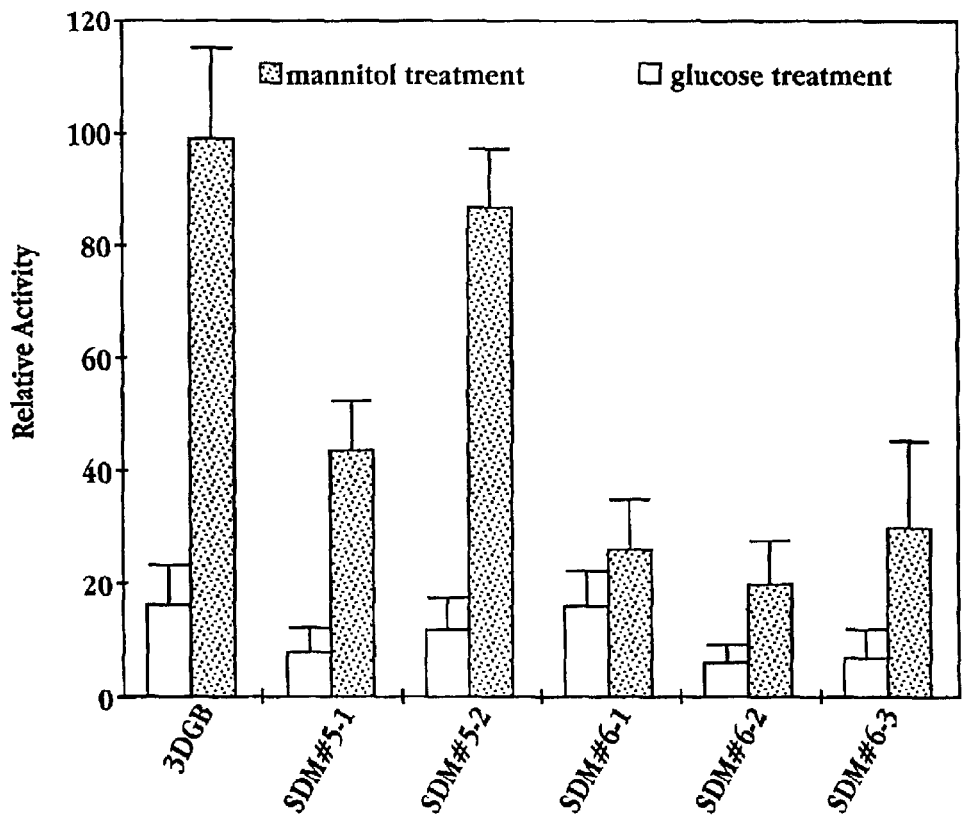
FIG. 5B shows levels of transient GUS expression observed in mannitol-treated (dark bars) and glucose-treated (light bars) rice protoplasts transformed with an expression plasmid containing each of the mutations shown in FIG. 5A.

The region −165 to −146, which contains the SDM5 and SDM6 sequence elements, was subjected to more detailed mutational analysis as shown in FIG. 5A. Within this region, a series of five SDM5 and SDM6 site-directed mutants were tested for GUS expression in the transient expression system, with the results shown in FIG. 5B. Significant reduction in GUS expression was observed in mutations of RAmy3D in the segment corresponding to SDM5-1 and in all of three of the SDM6 segments.

While the invention has been described with reference to specific methods and embodiments, it will be appreciated that various modifications and changes may be made without departing from the invention.

It is claimed:

1. A chimeric plant promoter for upregulating expression of a coding sequence operatively linked to the promoter, under conditions of sugar depletion or deprivation in a plant cell, comprising:
   (i) a promoter element effective to express the coding sequence in plant cells, under selected conditions, and
   (ii) carried in said promoter element, a heterologous sequence from the Amy3D promoter comprising SEQ ID NO:1, SEQ ID NO:2, SEQ ID NO:3, SEQ ID NO:4, SEQ ID NO:5 or combinations thereof.

2. The chimeric promoter of claim 1, wherein the heterologous sequence is identified by SEQ ID NO: 1.

3. The chimeric promoter of claim 1, wherein the heterologous sequence is identified by SEQ ID NO: 2.

4. The chimeric promoter of claim 1, wherein the heterologous sequence is identified by SEQ ID NO: 3.

5. The chimeric promoter of claim 1, wherein the heterologous sequence is identified by SEQ ID NO: 4.

6. The chimeric promoter of claim 1, wherein the heterologous sequence is SEQ ID NO: 5.

7. The chimeric promoter of claim 1, wherein the heterologous sequence is duplicated.

8. The chimeric promoter of claim 1, wherein the promoter element is from a monocot α-amylase gene selected from the group consisting of the RAmy1A, RAmy1B, RAmy2A, RAmy3A, RAmy3B, RAmy3C, pM/C, gKAmy141, gKAmy155, Amy32b, and HV18 genes.

9. A method of enhancing the inducibility by sugar depletion or deprivation of a plant or plant-virus promoter in plant cells, said method comprising:

introducing into a plant promoter or plant-virus promoter, a heterologous sequence from the Amy3D promoter comprising SEQ ID NO:1, SEQ ID NO:2, SEQ ID NO:3, SEQ ID NO:4, SEQ ID NO: 5 or combinations thereof, by said introducing, achieving at least a 2-fold greater sugar-depletion induction level of the promoter in plant cells over that of the unmodified promoter.

10. The method of claim 9, wherein the promoter element is from an α-amylase gene selected from the group consisting of the RAmy1A, RAmy1B, RAmy2A, RAmy3 A, RAmy3 B, RAmy3C, pM/C, gKAmy141, gKAmy155, Amy32b, and HV18 genes.

11. The method of claim 9, wherein the heterologous sequence is duplicated in the chimeric promoter.

12. The method of claim 9, wherein the plant promoter is from a monocot plant.

13. A vector for use in tranforming a plant, comprising:

a chimeric gene having, operatively linked in sequence in a 5' to 3' direction, (i) the chimeric plant promoter of claim 1, (ii) a gene encoding a protein to be expressed, and (iii) a 3' untranslated terminator region.

14. Plant cells transformed with the vector of claim 13.

15. The plant cells of claim 14, which are monocot cells.

* * * * *

SEQUENCE LISTING (1) GENERAL INFORMATION:

(iii) NUMBER OF SEQUENCES: 21

(2) INFORMATION FOR SEQ ID NO: 1:

(i) SEQUENCE CHARACTERISTICS:
      (A) LENGTH: 42 base pairs
      (B) TYPE: nucleic acid
      (C) STRANDEDNESS: single
      (D) TOPOLOGY: linear (xi) SEQUENCE DESCRIPTION: SEQ ID NO: 1:

CGACGCGGCG CCTACGTGGC CATGCTTTAT TGCCTTATCC AT       42

(2) INFORMATION FOR SEQ ID NO: 2:

(i) SEQUENCE CHARACTERISTICS:
      (A) LENGTH: 10 base pairs
      (B) TYPE: nucleic acid
      (C) STRANDEDNESS: single
      (D) TOPOLOGY: linear (xi) SEQUENCE DESCRIPTION: SEQ ID NO: 2:

CGACGCGGCG       10

(2) INFORMATION FOR SEQ ID NO: 3:

(i) SEQUENCE CHARACTERISTICS:
      (A) LENGTH: 9 base pairs
      (B) TYPE: nucleic acid
      (C) STRANDEDNESS: single
      (D) TOPOLOGY: linear (xi) SEQUENCE DESCRIPTION: SEQ ID NO: 3:

CTACGTGGC       9

(2) INFORMATION FOR SEQ ID NO: 4:

(i) SEQUENCE CHARACTERISTICS:
      (A) LENGTH: 8 base pairs
      (B) TYPE: nucleic acid
      (C) STRANDEDNESS: single
      (D) TOPOLOGY: linear (xi) SEQUENCE DESCRIPTION: SEQ ID NO: 4:

TTATCCAT       8

(2) INFORMATION FOR SEQ ID NO: 5:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (xi) SEQUENCE DESCRIPTION: SEQ ID NO: 5:

CGACGCGGCG CCTACGTGGC       20

(2) INFORMATION FOR SEQ ID NO: 6:

(i) SEQUENCE CHARACTERISTICS:
      (A) LENGTH: 110 base pairs
      (B) TYPE: nucleic acid
      (C) STRANDEDNESS: single (D) TOPOLOGY: linear (xi) SEQUENCE DESCRIPTION: SEQ ID NO: 6:

CGCCGCATCC CGTCGCCTTG GAGACCGGGC CCCGACGCGG CCGACGCGGC GCCTACGTGG     60

CCATGCTTTA TTGCCTTATC CATATCCACG CCATTTATTG TGGTCGTCTC                110

(2) INFORMATION FOR SEQ ID NO: 7:

(i) SEQUENCE CHARACTERISTICS:
        (A) LENGTH: 110 base pairs
        (B) TYPE: nucleic acid
        (C) STRANDEDNESS: single
        (D) TOPOLOGY: linear (xi) SEQUENCE DESCRIPTION: SEQ ID NO: 7:

GAATTCCGAG CGTCGCCTTG GAGACCGGGC CCCGACGCGG CCGACGCGGC GCCTACGTGG     60

CCATGCTTTA TTGCCTTATC CATATCCACG CCATTTATTG TGGTCGTCTC                110

(2) INFORMATION FOR SEQ ID NO: 8:

(i) SEQUENCE CHARACTERISTICS:
        (A) LENGTH: 110 base pairs
        (B) TYPE: nucleic acid
        (C) STRANDEDNESS: single
        (D) TOPOLOGY: linear (xi) SEQUENCE DESCRIPTION: SEQ ID NO: 8:

CGCCGCATCC ATGAATTCGT GAGACCGGGC CCCGACGCGG CCGACGCGGC GCCTACGTGG     60

CCATGCTTTA TTGCCTTATC CATATCCACG CCATTTATTG TGGTCGTCTC                110

(2) INFORMATION FOR SEQ ID NO: 9:

(i) SEQUENCE CHARACTERISTICS:
        (A) LENGTH: 110 base pairs
        (B) TYPE: nucleic acid
        (C) STRANDEDNESS: single
        (D) TOPOLOGY: linear (xi) SEQUENCE DESCRIPTION: SEQ ID NO: 9:

CGCCGCATCC CGTCGCCTTG TCTGAATTCA ACCGACGCGG CCGACGCGGC GCCTACGTGG     60

CCATGCTTTA TTGCCTTATC CATATCCACG CCATTTATTG TGGTCGTCTC                110

(2) INFORMATION FOR SEQ ID NO: 10:

(i) SEQUENCE CHARACTERISTICS:
        (A) LENGTH: 110 base pairs
        (B) TYPE: nucleic acid
        (C) STRANDEDNESS: single
        (D) TOPOLOGY: linear (xi) SEQUENCE DESCRIPTION: SEQ ID NO: 10:

CGCCGCATCC CGTCGCCTTG GAGACCGGGC CAATGAATTC ACGACGCGGC GCCTACGTGG     60

CCATGCTTTA TTGCCTTATC CATATCCACG CCATTTATTG TGGTCGTCTC                110

(2) INFORMATION FOR SEQ ID NO: 11:

(i) SEQUENCE CHARACTERISTICS:
        (A) LENGTH: 110 base pairs
        (B) TYPE: nucleic acid
        (C) STRANDEDNESS: single
        (D) TOPOLOGY: linear (xi) SEQUENCE DESCRIPTION: SEQ ID NO: 11:

```
CGCCGCATCC CGTCGCCTTG GAGACCGGGC CCCGACGCGG CAAGTACTTA TCCTACGTGG      60

CCATGCTTTA TTGCCTTATC CATATCCACG CCATTTATTG TGGTCGTCTC                 110

(2) INFORMATION FOR SEQ ID NO: 12:

(i) SEQUENCE CHARACTERISTICS:
        (A) LENGTH: 110 base pairs
        (B) TYPE: nucleic acid
        (C) STRANDEDNESS: single
        (D) TOPOLOGY: linear (xi) SEQUENCE DESCRIPTION: SEQ ID NO: 12:

CGCCGCATCC CGTCGCCTTG GAGACCGGGC CCCGACGCGG CCGACGCGGC GCAGTACTTT      60

ACATGCTTTA TTGCCTTATC CATATCCACG CCATTTATTG TGGTCGTCTC                 110

(2) INFORMATION FOR SEQ ID NO: 13:

(i) SEQUENCE CHARACTERISTICS:
        (A) LENGTH: 110 base pairs
        (B) TYPE: nucleic acid
        (C) STRANDEDNESS: single
        (D) TOPOLOGY: linear (xi) SEQUENCE DESCRIPTION: SEQ ID NO: 13:

CGCCGCATCC CGTCGCCTTG GAGACCGGGC CCCGACGCGG CCGACGCGGC GCCTACGTGG      60

CCCGTGAATT CGTACTTATC CATATCCACG CCATTTATTG TGGTCGTCTC                 110

(2) INFORMATION FOR SEQ ID NO: 14:

(i) SEQUENCE CHARACTERISTICS:
        (A) LENGTH: 110 base pairs
        (B) TYPE: nucleic acid
        (C) STRANDEDNESS: single
        (D) TOPOLOGY: linear (xi) SEQUENCE DESCRIPTION: SEQ ID NO: 14:

CGCCGCATCC CGTCGCCTTG GAGACCGGGC CCCGACGCGG CCGACGCGGC GCCTACGTGG      60

CCATGCTTTA TTGCCGAGTA CTGATCCACG CCATTTATTG TGGTCGTCTC                 110

(2) INFORMATION FOR SEQ ID NO: 15:

(i) SEQUENCE CHARACTERISTICS:
        (A) LENGTH: 110 base pairs
        (B) TYPE: nucleic acid
        (C) STRANDEDNESS: single
        (D) TOPOLOGY: linear (xi) SEQUENCE DESCRIPTION: SEQ ID NO: 15:

CGCCGCATCC CGTCGCCTTG GAGACCGGGC CCCGACGCGG CCGACGCGGC GCCTACGTGG      60

CCATGCTTTA TTGCCTTATC CATATCAAGT ACTTTTATTG TGGTCGTCTC                 110

(2) INFORMATION FOR SEQ ID NO: 16:

(i) SEQUENCE CHARACTERISTICS:
        (A) LENGTH: 110 base pairs
        (B) TYPE: nucleic acid
        (C) STRANDEDNESS: single
        (D) TOPOLOGY: linear (xi) SEQUENCE DESCRIPTION: SEQ ID NO: 16:

CGCCGCATCC CGTCGCCTTG GAGACCGGGC CCCGACGCGG CCGACGCGGC GCCTACGTGG      60

CCATGCTTTA TTGCCTTATC CATATCCACG CCAGGGCGAA TTCTCGTCTC                 110
```

(2) INFORMATION FOR SEQ ID NO: 17:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 17:

GAATTCGGCG CCTACGTGGC     20

(2) INFORMATION FOR SEQ ID NO: 18:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 18:

CGACGGGATC CCTACGTGGC     20

(2) INFORMATION FOR SEQ ID NO: 19:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 19:

CGACGCGGCG CTCGAGTGGC     20

(2) INFORMATION FOR SEQ ID NO: 20:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 20:

CGACGCGGCG CCTACCATGG     20

(2) INFORMATION FOR SEQ ID NO: 21:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 21:

CGACGCGGCG CCGCATGCGC     20